United States Patent
Tirosh et al.

(10) Patent No.: US 7,394,531 B2
(45) Date of Patent: Jul. 1, 2008

(54) APPARATUS AND METHOD FOR AUTOMATIC OPTICAL INSPECTION

(75) Inventors: Ehud Tirosh, Mevaseret Zion (IL); Boaz Kenan, Portland, OR (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 11/554,280

(22) Filed: Oct. 30, 2006

(65) Prior Publication Data
US 2007/0159623 A1 Jul. 12, 2007

Related U.S. Application Data

(63) Continuation-in-part of application No. 11/047,435, filed on Jan. 31, 2005.

(51) Int. Cl.
*G01N 21/00* (2006.01)
(52) U.S. Cl. ............... 356/237.1; 250/234; 250/310; 250/208.1; 356/237.2; 356/398; 356/600
(58) Field of Classification Search ...... 356/237–237.5, 356/398, 600–605; 250/234, 310, 208.1
See application file for complete search history.

(56) References Cited

U.S. PATENT DOCUMENTS 6,177,954 B1 * 1/2001 Bouvier .................. 348/92
7,109,464 B2 * 9/2006 Cartlidge et al. ......... 250/208.1
7,122,786 B2 * 10/2006 Tochio et al. ................ 250/234
2001/0012107 A1 * 8/2001 Toh ............................ 356/601

* cited by examiner

*Primary Examiner*—Layla G. Lauchman
*Assistant Examiner*—Iyabo S Alli
(74) *Attorney, Agent, or Firm*—Patterson & Sheridan LLP (57) ABSTRACT

An automated optical inspection system, comprising at least one camera having a field of view; and at least one image scanning module comprising a plurality of objective modules arranged to have fields of view covering a portion of an article during inspection, and an image selection mirror mechanism, such as a pentaprism movable to sequentially select and transfer images of the fields of view from the objective modules to the at least one camera, and a beam splitter operative to simultaneously direct illumination from at least one illumination source to a portion of the article and to direct an image of the portion of the article to at least one camera, wherein the beam splitter is operative to pivot about at least one axis, thereby to create motion of the image of the article within the field of view of the camera. The objective modules may be arranged in a pair of back-to-back arcs each served by and partially encircling its own optical head. The image selection mirror mechanism may be rotated by a rotating shaft having a driving end, the mechanism being disposed between the shaft's driving end, and the article.

20 Claims, 6 Drawing Sheets

APPARATUS AND METHOD FOR AUTOMATIC OPTICAL INSPECTION

REFERENCE TO CO-PENDING APPLICATIONS

This application is a continuation-in-part of U.S. Ser. No. 11/047,435, entitled "Automatic optical inspection using multiple objectives", filed 31 Jan. 2005 and published 3 Aug. 2006, the disclosure of which is hereby incorporated by reference.

FIELD OF THE INVENTION

The present invention relates generally to apparatus and methods for automatic optical inspection.

BACKGROUND OF THE INVENTION

A wide variety of automatic optical inspection systems are known, such as those described in copending US Published Application No. 2006/0170910 A1, published less than one year ago, on 3 Aug. 2006.

The disclosures of all publications and patent documents mentioned in the specification, and of the publications cited therein directly or indirectly, are hereby incorporated by reference.

SUMMARY OF THE INVENTION

The present invention seeks to provide an improved automatic optical inspection system.

There is thus provided, in accordance with a preferred embodiment of the present invention, an automated optical inspection system, comprising a light source; at least one camera having a field of view; and at least one image scanning module comprising a plurality of objective modules arranged to have fields of view covering a portion of an article during inspection; and an image selection mirror mechanism movable to sequentially select and transfer images of the fields of view from the objective modules to the at least one camera; and a beam splitter operative to simultaneously direct illumination from at least one illumination source to a portion of the article and to direct an image of the portion of the article to the at least one camera, wherein the beam splitter is operative to pivot about at least one axis, thereby to create motion of the image of the article within the field of view of the camera.

Further in accordance with a preferred embodiment of the present invention, the beam splitter pivots about an axis, y, which is perpendicular to a first light path extending between the light source and the beam splitter and also perpendicular to a second light path extending between the beam splitter and the camera.

Still further in accordance with a preferred embodiment of the present invention, the beam splitter pivots about an axis, z, which is parallel to a first light path extending between the light source and the beam splitter.

Further in accordance with a preferred embodiment of the present invention, the plurality of objective modules is arranged in at least one pair of arcs.

Still further in accordance with a preferred embodiment of the present invention, the article comprises a wafer and the at least one pair of arcs comprises two back-to-back arcs each partially encircling and served by its own optical head.

Further in accordance with a preferred embodiment of the present invention, the pivot of the beam splitter generates motion of the image relative to the camera along an axis parallel to the scanning direction.

Additionally in accordance with a preferred embodiment of the present invention, pivot of the beam splitter generates motion of the image relative to the camera in a direction perpendicular to the scanning direction.

Additionally in accordance with a preferred embodiment of the present invention, the image selection mirror mechanism causes at least one image to move, during image capture, in a first direction within the field of view of the camera, wherein the at least one camera comprises at least one generally planar sensor defining an operative plane and wherein the system also comprises apparatus for moving the at least one sensor within the operative plane, during image capture, in the first direction.

Further in accordance with a preferred embodiment of the present invention, at least one image of the article moves within the field of view of the camera at a non-uniform velocity.

Also provided, in accordance with another preferred embodiment or the present invention, is an automated optical inspection system, comprising at least one camera having a field of view; and at least one image scanning module comprising a plurality of objective modules arranged to have fields of view covering a portion of an article during inspection and an image selection mirror mechanism movable to sequentially select and transfer images of the fields of view from the objective modules to the at least one camera, wherein the at least one image scanning module comprises at least one pair of image scanning modules defining at least one pair of arcs including first and second arcs and wherein the first arc is arranged back to back relative to the second arc.

Further provided, in accordance with still another preferred embodiment of the present invention, is an automated optical inspection system, comprising at least one camera having a field of view; and at least one image scanning module comprising a plurality of objective modules arranged to have fields of view covering a portion of an article during inspection and an image selection mirror mechanism movable to sequentially select and transfer images of the fields of view from the objective modules to the at least one camera, wherein the image selection mirror mechanism comprises a double-reflecting optical element.

Further in accordance with a preferred embodiment of the present invention, the double-reflecting optical element comprises a pentaprism.

Also provided, in accordance with yet another preferred embodiment of the present invention, is an automated optical inspection system, comprising at least one camera having a field of view; and at least one image scanning module comprising a plurality of objective modules arranged to have fields of view covering a portion of an article during inspection and an image selection mirror mechanism movable to sequentially select and transfer images of the fields of view from the objective modules to the at least one camera, thereby to define an optical path, wherein the image selection mirror mechanism is rotated by a rotating shaft having a first end providing rotation of the mechanism, the image selection mirror mechanism being disposed between the first end of the shaft, and the article.

Further in accordance with a preferred embodiment of the present invention, the at least one pair of arcs comprises a single pair of arcs and wherein the fields of view of the pair of arcs together cover the entirety of the relevant surface area of the article and wherein the image scanning module also comprises first and second optical heads partially encircled by the first and second arcs respectively.

Still further in accordance with a preferred embodiment of the present invention, at least one pair of arcs comprises first and second arcs arranged back to back.

Further in accordance with a preferred embodiment of the present invention, the plurality of objective modules is arranged in two arcs arranged back to back.

Still further in accordance with a preferred embodiment of the present invention, the image selection mirror mechanism comprises a double-reflecting optical element.

Further in accordance with a preferred embodiment of the present invention, the double-reflecting optical element comprises a pentaprism.

Further in accordance with a preferred embodiment of the present invention, the article is scanned in a scanning direction and the camera moves parallel to the scanning direction.

Also provided, in accordance with another embodiment of the invention, is an automated optical inspection system, comprising at least one camera having a field of view; and at least one image scanning module comprising a plurality of objective modules arranged to have fields of view covering a portion of an article during inspection and an image selection mirror mechanism movable to sequentially select and transfer images of the fields of view from the objective modules to the at least one camera, wherein at least one camera comprises at least one generally planar sensor defining an operative plane and wherein the system also comprises apparatus for moving at least one sensor within the operative plane, during image capture, in a direction opposite to the direction of motion of the image within the field of view of the camera caused by operation of the image selection mirror mechanism.

Further provided, in accordance with still another embodiment of the invention, is a method for inspecting an article, comprising bringing at least a portion of the article into fields of view of at least one of a plurality of objective modules, adjusting an image selection mirror mechanism to sequentially direct images of the field of view from the objective modules to at least one camera which is shared by the objective modules and which has a field of view, capturing the images with the shared camera, and processing the captured images to detect defects in the article, wherein at least one image of the article moves within the field of view of the camera at a non-uniform velocity.

BRIEF DESCRIPTION OF THE DRAWINGS

Preferred embodiments of the present invention are illustrated in the following drawings.

DETAILED DESCRIPTION OF PREFERRED EMBODIMENTS

Figure 1:
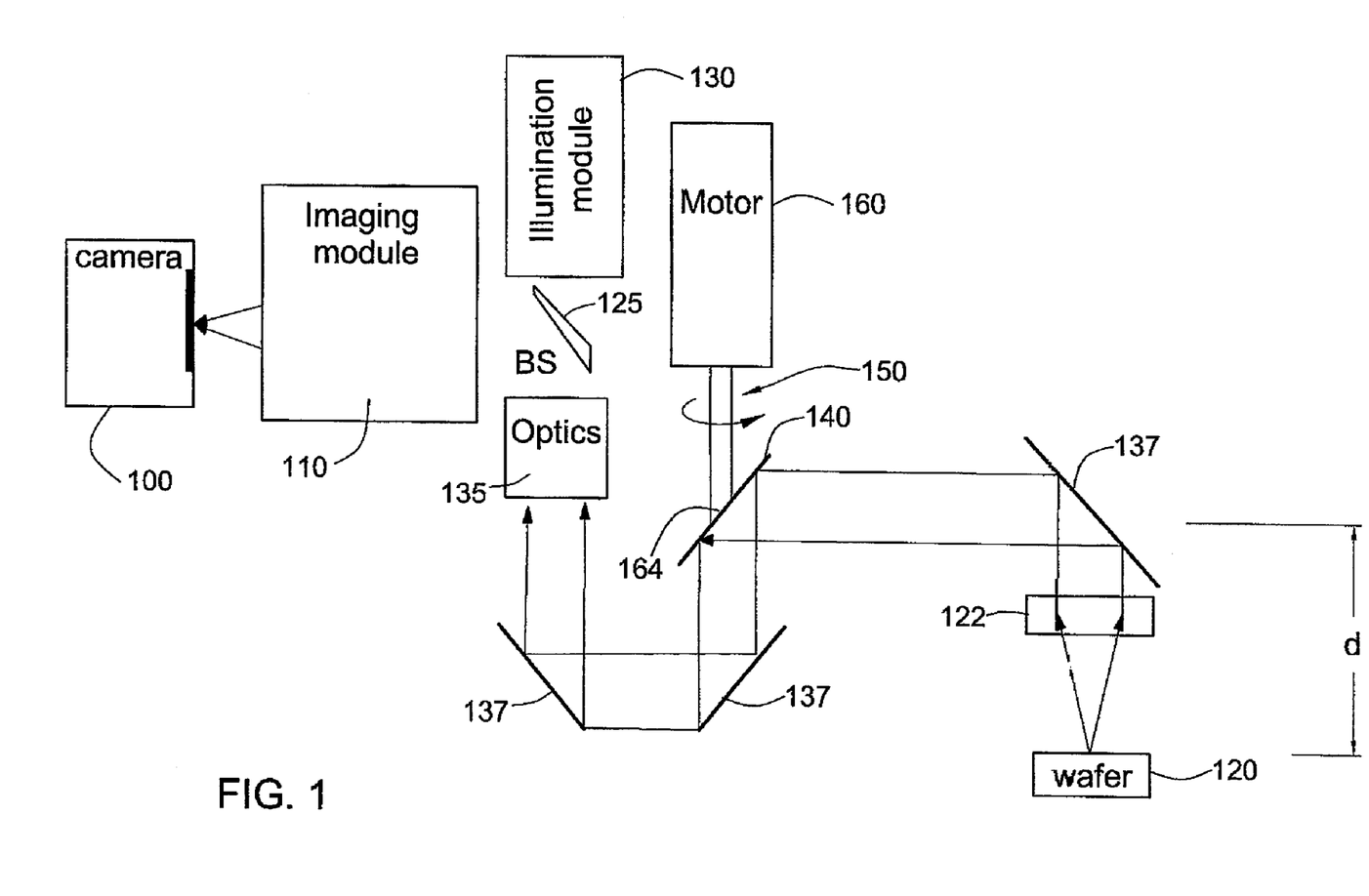
FIG. 1 is a simplified semi-block, semi-side view illustration of an automated optical inspection system constructed and operative In accordance with respective preferred embodiments of the present invention.

Reference is now made to FIG. 1 which is a simplified optical diagram of an automated optical inspection system constructed and operative in accordance with a preferred embodiment of the present invention. For simplicity, a portion of the light path which is particularly relevant to the embodiment, is shown and other portions of the light path are omitted.

The system of FIG. 1 includes at least one camera 100, such as a CCD camera, having a field of view and at least one image scanning module 110, also termed herein an "imaging module". The system of FIG. 1 and typically comprises a plurality of objective modules arranged to have fields of view covering a portion of an article e.g. wafer 120 during inspection thereof, however for simplicity, only one of the objective modules is shown. The wafer is typically positioned in operative association with an objective 122. The camera 100 and image scanning module 110 are operatively associated with a beam splitter 125, an illumination module 130 which may comprise a flash lamp having a 2 mm*1 mm arc, conventional optics 135, and conventional, suitably placed mirrors 137. An image selection mirror mechanism 140 is movable to sequentially select and transfer images of the fields of view from the objective module/s to the at least one camera 100. As shown, the image selection mirror mechanism 140 is rotated by a rotating shaft 150 powered by a motor 160. As shown, the mechanism 140 is typically located between the driving end 164 of the rotating shaft, and the article 120.

The embodiment of FIG. 1 is advantageous because if it is desired to restrict the number of optical heads insofar as possible, the system's resolution is limited by the ratio between the field of view and the diameter of the objective. The diameter of the objective increases as a function of the numerical aperture and as a function of the objective's focal length. Shortening the focal length either reduces the objective diameter, thereby to increase the number of objectives per optical head i.e. decrease the total number of optical heads, or maintains the objective diameter thereby to enhance the system's resolution by increasing the numerical aperture.

In the embodiment shown in the above-referenced copending published US application, the focal length has a lower bound which is determined by the size of the motor since the motor size in turn determines the height of the objective above the wafer this is when we do not use the inverted motor. Since it is desirable to position the objectives as close to the wafer as possible, the embodiment illustrated herein, in FIG. 1, in which the motor is inverted, is seen to be advantageous in reducing the focal length of the objective.

Figure 2:
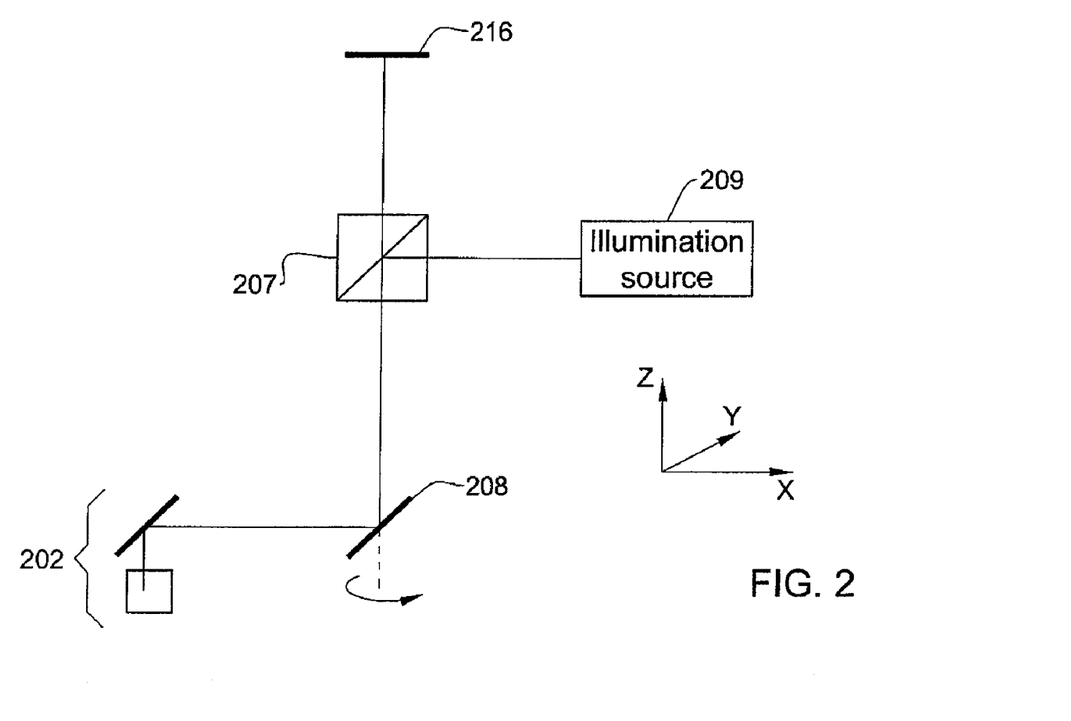
FIG. 2 is a simplified side-view illustration of the apparatus of FIGS. 3A-3D in Published Application No. US 2006/0170910 A1.

Reference is now made to FIG. 2 which is similar to the apparatus shown in FIGS. 3A-3D of Published Application No. US 2006/0170910 A1, although for simplicity, in FIG. 2, a plurality of objective modules ($202_i$ in the published application) are represented by a single objective module, 202 in FIG. 2. A particular feature of the embodiment of FIG. 2 is that an image selection mirror 208 rotates around a z axis to sequentially select between the plurality of objective modules of which one, 202, is shown.

Figure 3:
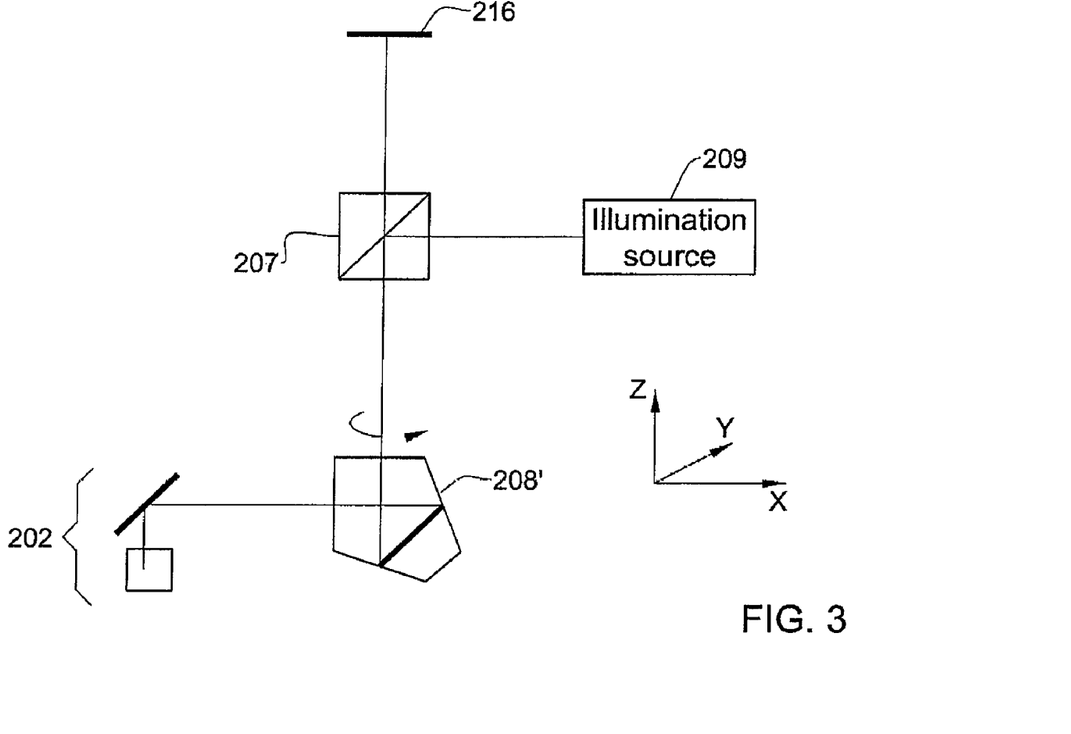
FIG. 3 is a simplified side-view illustration of apparatus, including a pentaprism for transferring images from one objective module to another, constructed and operative in accordance with a preferred embodiment of the invention.

A disadvantage of the embodiment illustrated in FIG. 2 is that the rotating mirror shown by way of example is relied upon to deflect the illumination and imaging path from a vertical, z, direction to a horizontal scanning path located in the x-y plane, using a changing angle theta. However, in practice, instability of the motor, such as wobble, may result in the beam being deflected to a location external to the x-y plane, because the deflection angle deviates slightly from 90 degrees due to the wobble. Therefore, as shown in FIG. 3, the image selection mirror 208 may be replaced by a pentaprism 208', in order to decrease or even eliminate the impact of accidental rotation of the image selection mirror around its y axis, which may be caused by motor wobble, for example. The pentaprism, unlike the rotating mirror, deflects light at 90 degrees unaffected by wobble error. The pentaprism 208' also rotates about the z axis.

Figure 4:
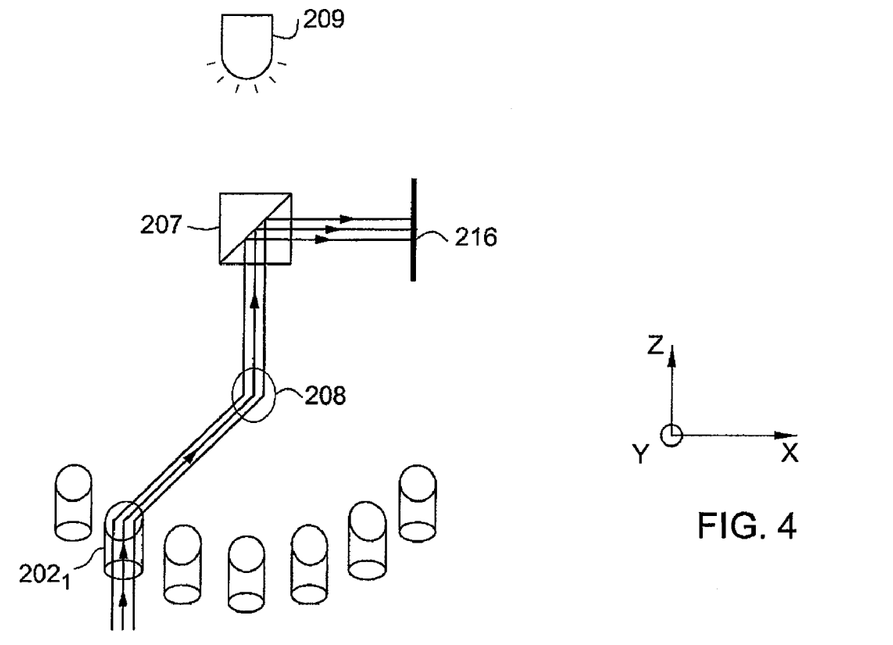
FIG. 4 is a simplified illustration of apparatus for transferring images from one objective module to another, so as to minimize motion of the object or image of the object relative to the imaging device, in accordance with another preferred embodiment of the invention.

FIG. 4 is a modification of FIG. 3B of the above-referenced copending published US Application, in which the roles of the illumination source 209 and the image plane of the camera 216 are reversed so as to provide image motion compensation during image capture, as described in detail hereinbelow. At least two types of compensation, or "canceling out", may be used to minimize this motion: compensation for motion of stage (by providing "canceling" motion in the opposite direction), and compensation for rotational motion of image selection mirror 208 (similarly, by providing "canceling" rotational motion in the opposite direction. When the latter compensation is provided, it may not be necessary to completely stop rotation of the image selection mirror prior to image capture.

When compensation for stage motion is provided, since the stage is moving along the y axis, compensation may involve translation of the image plane 216 along the y axis, and/or rotation of the beam splitter 207 around its z axis as in the illustrated embodiments. The translational and/or rotational velocities depend on the exact optical design and can be computed by one skilled at the art.

When compensation for the rotation of the image selection mirror 208 is provided, since image motion is along the x axis, which, in the camera 216, translates to the z axis, compensation may involve translation of the camera 216 (FIG. 4) along the z axis and/or beam splitter rotation around the y axis. The translational and/or rotational velocities depend on the exact optical design and can be computed by one skilled at the art.

Figure 5:
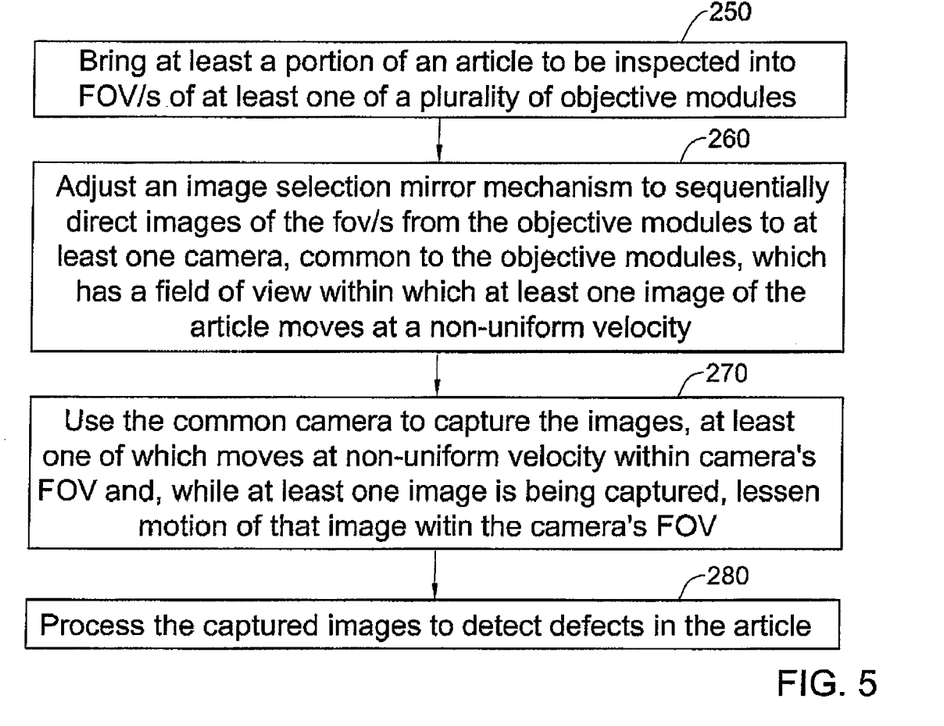
FIG. 5 is a simplified flowchart illustration of an automatic optical inspection method constructed and operative in accordance with an embodiment of the invention.

Methods and apparatus for performing automatic optical inspection (AOI) while reducing, minimizing or eliminating motion of the object or image of the object relative to the imaging device, during image capture, are described in U.S. patent application Ser. No. 11/549,059 filed Oct. 12 2006 and in the self-explanatory flowchart of FIG. 5.

Figure 6:
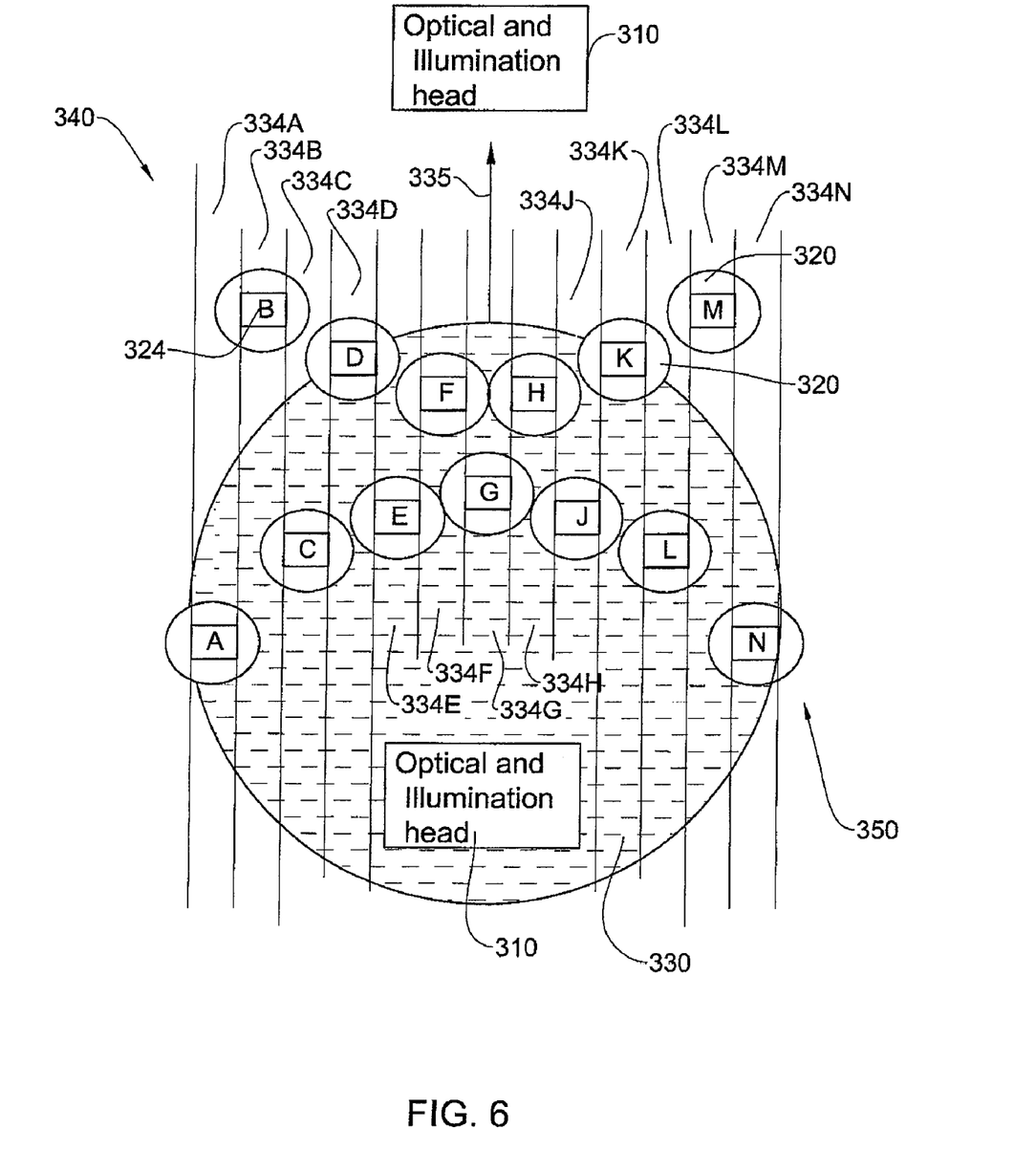
FIG. 6 is a simplified pictorial illustration of automated optical inspection apparatus for round objects such as wafers, including a plurality of objective modules arranged in at least one pair of back-to-back arcs.

Reference is now made to FIG. 6 which schematically illustrates an automated optical inspection system particularly suitable for inspecting wafers and other similarly sized objects. The system of FIG. 6 comprises at least one camera having a field of view, whose optical and illumination heads 310 are shown, at least one image scanning module comprising a plurality of objective modules 320 arranged to have fields of view 324 covering a portion of a wafer 330 during inspection and an image selection mirror mechanism movable to sequentially select and transfer images of the fields of view from the objective modules to the at least one camera. The image scanning module defines at least one pair of arcs including first and second arcs 340 and 350. The first arc 340 is arranged back to back relative to the second arc 350, as in FIG. 2A of the above-referenced copending published US patent application. Preferably, for wafer inspection applications, exactly two back-to-back arcs are provided, each encircling, and "served" by, its own optical and illumination head such that the number of optical and illumination heads 310 is preferably also exactly two.

A particular advantage of the configuration of FIG. 6 is that in other configurations, a wafer scan begins only when the leading arc encounters the leading rounded edge of the wafer and ends only when the following arc or second arc finishes scanning the rear rounded edge of the wafer. In the configuration of FIG. 6, the arc configuration corresponds to the configuration of the wafer's edges and the distance between arcs is shorter thereby significantly decreasing wafer scan time, perhaps by as much as 50%. It is appreciated that unlike in flat panel display inspection applications in which the translation speed of the inspected plates is determined by production line considerations, in wafer inspection applications, translation speed of the inspected object or wafer is a function of inspection speed.

Typically, the relationship between the wafer's diameter and the x and y dimensions, FOVx and FOVy, respectively, of the fields of view of the objective modules 320, is approximately 12:8.

As illustrated, the surface area of wafer 330 may be conceptually divided into adjacent columns 334A, 334B, . . . disposed along the scanning direction 335, with the odd and even columns being covered by the two arcs respectively i.e. adjacent columns are typically not covered by the same arc. In the illustrated embodiment, columns 334A-334N are respectively imaged by objective modules A-N respectively, where modules B, D, F, H, K and M form the top arc 340 whereas modules A, C, E, G, J, L and N form the bottom arc 350.

It is appreciated that, as shown in FIGS. 5C-5E of the above-referenced copending published US application, the) (configuration of the back-to-back arcs of FIG. 6 may be replaced by "parallel arcs" having a ((configuration in which both arcs face in the same direction, typically in the direction of motion of the wafer. However, care must be taken to ensure that the optics of each arc does not block the line of sight of the other arc.

Figure 7:
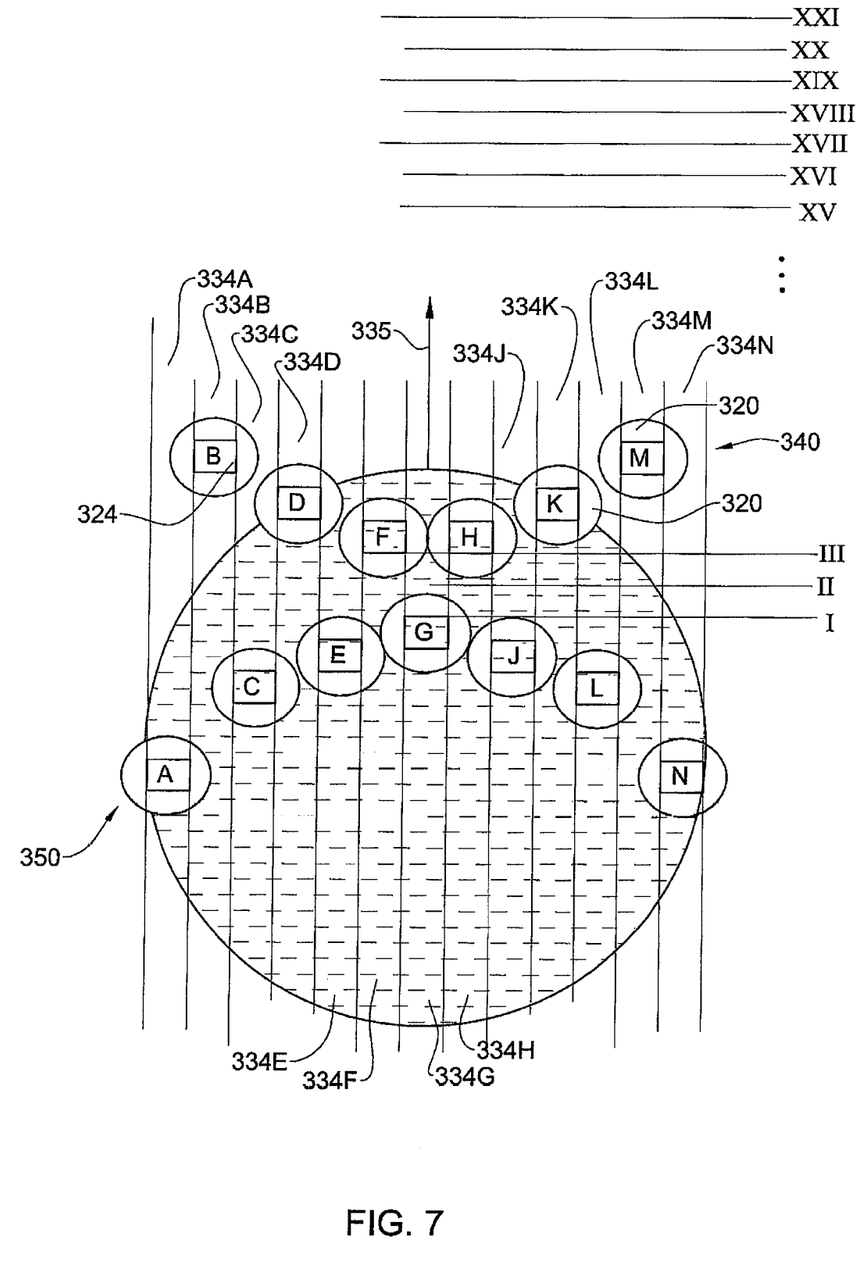
FIG. 7 is a simplified pictorial illustration of a plurality of scanning positions of the apparatus of FIG. 6.
Figure 8:
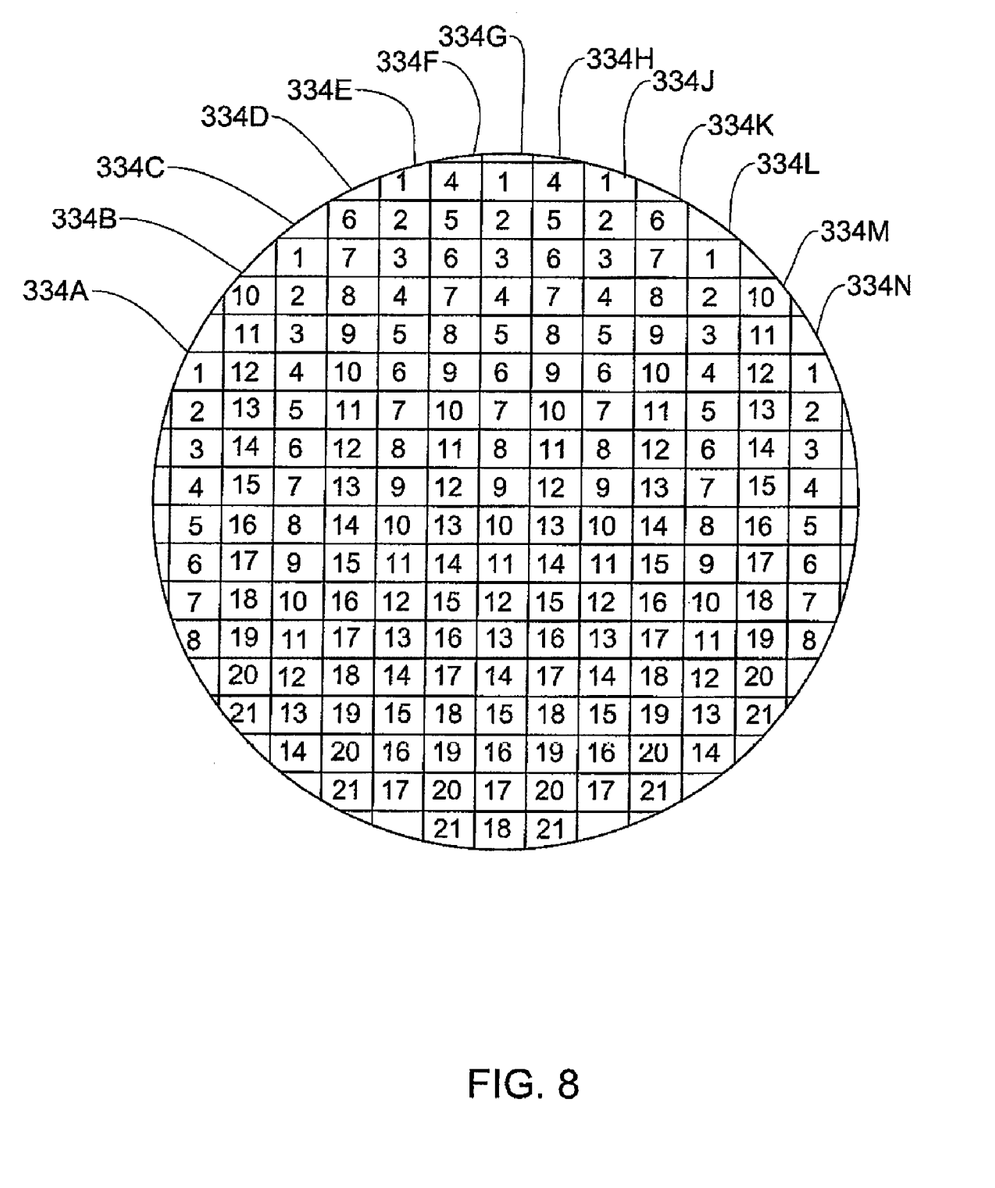
FIG. 8 is a simplified pictorial illustration of a round object being scanned by the apparatus of FIG. 6, including indications of the position at which the apparatus of FIG. 6 is disposed, as each particular portion of the surface area of the round object undergoes scanning.

FIG. 7 illustrates a sequence of positions of the wafer along the scanning direction, as indicated by Roman reference numerals I-XXI, the distance between these positions, along the scanning direction, typically comprising the y-dimension of the module's field of view (FOVy). In FIG. 7, the optical and illumination heads 310 of FIG. 4 are eliminated for simplicity. FIG. 8 indicates, for each field-of-view sized location within the columns 134A-334N, the position occupied by the wafer 330 when that location is imaged. For example, the upper edge of the column 334A is imaged (by module A) when the wafer 330 is in position I, and the lower edge when the wafer is in position IX. The upper edge of column 334C, which is longer, is also imaged (by module C) when the wafer is in position I, and the lower image when the wafer is in position 15 (XV), and by the time the wafer has reached position 19 (XIX), the columns "belonging to" the bottom arc have been, completed. Very soon after scanning begins (position I), the upper arc 112A has already begun its operation. Initially (when the wafer is in Position IV), the modules closest to the middle (modules F and II in the illustrated embodiment) begin to scan, followed by modules D and K, e.g. when the wafer is in Positions 5 or 6 (V or VI) and subsequently B and M (e.g. when the wafer is in Position 9 or 10 (IX or X)). It is appreciated that by the time the wafer reaches Position 21 (XXI), approximately, even the columns "belonging" to the top arc have been completed, the last columns to be completed being the middle columns (F and H in the illustrated embodiment).

Features of the present invention which are described in the context of separate embodiments may also be provided in combination in a single embodiment. In particular, the embodiments of FIGS. 1, 2, 3, 4 and 6-8 can all be combined into a single embodiment, or any subset of them may be combined. Conversely, features of the invention which are described for brevity in the context of a single embodiment may be provided separately or in any suitable subcombination.

The invention claimed is:

1. An automated optical inspection system, comprising:
   a light source;
   at least one camera having a field of view; and
   at least one image scanning module comprising:
      a plurality of objective modules arranged to have fields of view covering a portion of an article during inspection; and
      an image selection mirror mechanism movable to sequentially select and transfer images of the fields of view from the objective modules to the at least one camera; and
   a beam splitter operative to simultaneously direct illumination from at least one illumination source to a portion of the article and to direct an image of the portion of the article to said at least one camera,
   wherein said beam splitter is operative to pivot about at least one axis, thereby to create motion of the image of the article within the field of view of the camera.

2. The system according to claim 1 wherein said beam splitter pivots about an axis, y, which is perpendicular to a first light path extending between the light source and the beam splitter and also perpendicular to a second light path extending between the beam splitter and the camera.

3. The system according to claim 1 wherein said beam splitter pivots about an axis, z, which is parallel to a first light path extending between the light source and the beam splitter.

4. The system according to claim 1 wherein said plurality of objective modules is arranged in at least one pair of arcs.

5. The system according to claim 4 wherein said article comprises a wafer and said at least one pair of arcs comprises two back-to-back arcs each partially encircling and served by its own optical head.

6. The system according to claim 3 wherein the pivot of the beam splitter generates motion of the image relative to the camera along an axis parallel to the scanning direction.

7. The system according to claim 1 wherein pivot of the beam splitter generates motion of the image relative to the camera in a direction perpendicular to the scanning direction.

8. The system according to claim 1 wherein said image selection mirror mechanism causes at least one image to move, during image capture, in a first direction within the field of view of the camera, wherein said at least one camera comprises at least one generally planar sensor defining an operative plane and wherein said system also comprises apparatus for moving said at least one sensor within said operative plane, during image capture, in said first direction.

9. The system according to claim 1 wherein at least one image of the article moves within the field of view of the camera at a non-uniform velocity.

10. An automated optical inspection system, comprising:
    at least one camera having a field of view; and
    at least one image scanning module comprising a plurality of objective modules arranged to have fields of view covering a portion of an article during inspection and an image selection mirror mechanism movable to sequentially select and transfer images of the fields of view from the objective modules to the at least one camera,
    wherein said at least one image scanning module comprises at least one pair of image scanning modules defining at least one pair of arcs including first and second arcs and wherein said first arc is arranged back to back relative to said second arc.

11. An automated optical inspection system, comprising:
    at least one camera having a field of view; and
    at least one image scanning module comprising a plurality of objective modules arranged to have fields of view covering a portion of an article during inspection and an image selection mirror mechanism movable to sequentially select and transfer images of the fields of view from the objective modules to the at least one camera,
    wherein said image selection mirror mechanism comprises a double-reflecting optical element.

12. The system according to claim 11 wherein said double-reflecting optical element comprises a pentaprism.

13. An automated optical inspection system, comprising:
    at least one camera having a field of view; and
    at least one image scanning module comprising a plurality of objective modules arranged to have fields of view covering a portion of an article during inspection and an image selection mirror mechanism movable to sequentially select and transfer images of the fields of view from the objective modules to the at least one camera, thereby to define an optical path,
    wherein said image selection mirror mechanism is rotated by a rotating shaft having a first end providing rotation of said mechanism, said image selection mirror mechanism being disposed between said first end of said shaft, and said article.

14. The system according to claim 10 wherein said at least one pair of arcs comprises a single pair of arcs and wherein the fields of view of the pair of arcs together cover the entirety of the relevant surface area of the article and wherein said image scanning module also comprises first and second optical heads partially encircled by said first and second arcs respectively.

15. The system according to claim 4 wherein at least one pair of arcs comprises first and second arcs arranged back to back.

16. The system according to claim 4 wherein said plurality of objective modules is arranged in two arcs arranged back to back.

17. The system according to claim 1 wherein said image selection mirror mechanism comprises a double-reflecting optical element.

18. The system according to claim 17 wherein said double-reflecting optical element comprises a pentaprism.

19. The system according to claim 10 wherein said image selection mirror mechanism comprises a double-reflecting optical element.

20. The system according to claim 1 wherein said article is scanned in a scanning direction and wherein said camera moves parallel to said scanning direction.

* * * * *